US008821533B2

(12) United States Patent
Newman et al.

(10) Patent No.: US 8,821,533 B2
(45) Date of Patent: Sep. 2, 2014

(54) DEVICE FOR MINIMALLY INVASIVE PLASTIC SURGERY LIFT PROCEDURE

(75) Inventors: Nathan Newman, Beverly Hills, CA (US); Umesh H. Patel, West Lafayette, IN (US); Bhavin Shah, West Lafayette, IN (US); Ryan Dempsey, Carmel, IN (US); Diana Gail Reynolds, Seattle, WA (US)

(73) Assignees: Cook Biotech Incorporated, West Lafayette, IN (US); Nathan Newman, Beverly Hills, CA (US)

( * ) Notice: Subject to any disclaimer, the term of this patent is extended or adjusted under 35 U.S.C. 154(b) by 518 days.

(21) Appl. No.: 12/774,980

(22) Filed: May 6, 2010

(65) Prior Publication Data
US 2010/0286793 A1 Nov. 11, 2010

Related U.S. Application Data

(60) Provisional application No. 61/175,823, filed on May 6, 2009.

(51) Int. Cl.
A61F 2/00 (2006.01)
A61K 38/18 (2006.01)
A61F 2/02 (2006.01)
A61F 2/04 (2013.01)

(52) U.S. Cl.
USPC .................. 606/213; 623/23.72; 424/423

(58) Field of Classification Search
CPC .................. A61B 2017/00792; A61F 2/0059; A61F 2/0077; A61N 2017/00792
USPC .................... 606/213–221; 623/23.72, 13.17; 424/422–426, 443–449
See application file for complete search history.

(56) References Cited

U.S. PATENT DOCUMENTS

| | | | |
|---|---|---|---|
| 5,217,494 A | 6/1993 | Coggins et al. | |
| 6,432,101 B1 | 8/2002 | Weber et al. | |
| 6,645,226 B1 | 11/2003 | Jacobs et al. | |
| 7,235,100 B2 * | 6/2007 | Martinek | 623/13.14 |
| 2004/0006353 A1 * | 1/2004 | Bosley et al. | 606/151 |
| 2004/0267309 A1 * | 12/2004 | Garvin | 606/217 |
| 2005/0220848 A1 * | 10/2005 | Bates | 424/443 |
| 2005/0261737 A1 * | 11/2005 | Sakura | 606/215 |
| 2006/0206139 A1 * | 9/2006 | Tekulve | 606/200 |
| 2006/0259119 A1 * | 11/2006 | Rucker | 623/1.11 |
| 2007/0098755 A1 * | 5/2007 | Patel et al. | 424/423 |
| 2009/0082816 A1 * | 3/2009 | Graham et al. | 606/301 |

(Continued)

OTHER PUBLICATIONS

Brochure Coapt Systems, Inc., Facial Rejuvenation Surgery, "the Coapt Endotine midface," 2005, 8 pages.

(Continued)

Primary Examiner — Julian Woo
Assistant Examiner — Shaun L David
(74) Attorney, Agent, or Firm — Woodard, Emhardt, Moriarty, McNett & Henry LLP

(57) ABSTRACT

Described are medical devices configured for use in cosmetic surgery. The medical devices include an elongate body member having a proximal end, a distal end, and a plurality of gaps defined therebetween. At least a portion of the body member is associated with one or more layers of a collagenous extracellular matrix (ECM) material. The elongate member can include one or more tissue engaging members. In preferred embodiments, the collagenous extracellular matrix material includes one or more native or non-native bioactive components.

31 Claims, 5 Drawing Sheets

(56) References Cited

U.S. PATENT DOCUMENTS

2009/0149876 A1* 6/2009 Patel et al. .................... 606/151
2009/0171440 A1* 7/2009 Carlson et al. ............... 623/1.15
2011/0093088 A1* 4/2011 Chen et al. ................. 623/23.72

OTHER PUBLICATIONS

Brochure, Covidien "Parietex ProGrip Mesh Open Inguinal Hernian Repair," 2008, 6 pages.

Brochure, Grams Surgical Sutures "A Novel Face-Lift Suspension System", undated, 2 pages.

Eremia, Sorin et al., "A Novel Face-Lift Suspension Suture and Inserting Instrument: the Use of Large Anchors Knotted into a Suture with an Attached Needle and an Inserting Device Allowing for Single Entry Point Placement of the Suspension Suture. Preliminary report of 20 Cases with 6 to 12 Month, Follow-Up" Dermatol. Surg. 2006;32:335-345; 2006.

Webpage, http://investor.com, Covidien Investor Relations News Release "Covidien Launches Parietex ProGrip Hernia Repair Mesh" last printed Oct. 22, 2008, 1 page.

* cited by examiner

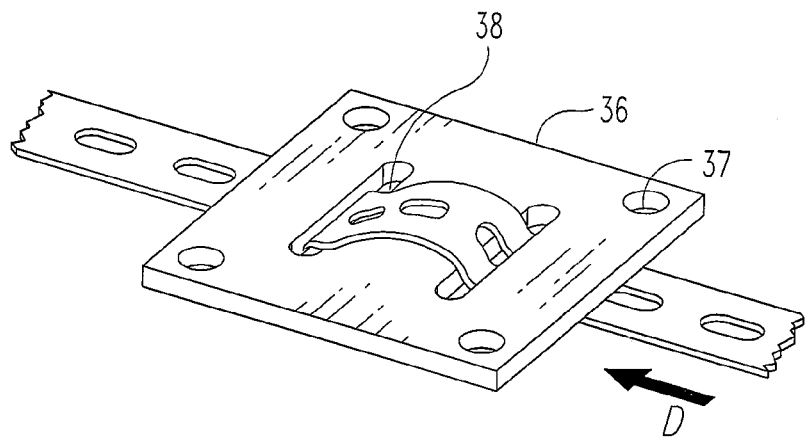
Fig. 3
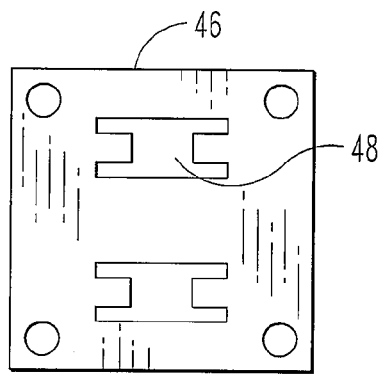 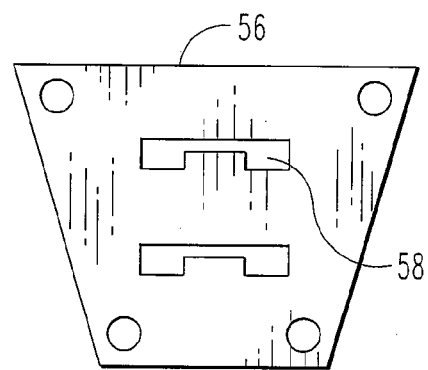
Fig. 4A             Fig. 4B
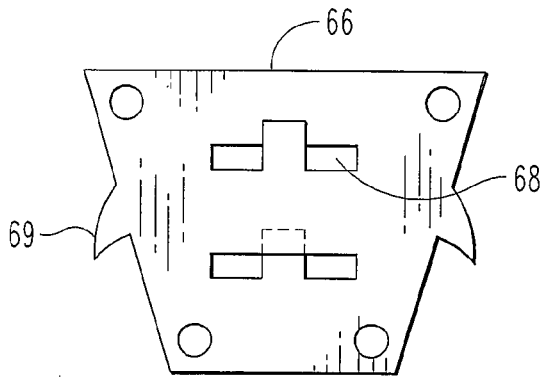 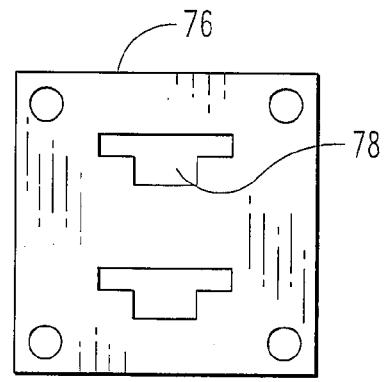
Fig. 4C             Fig. 4D

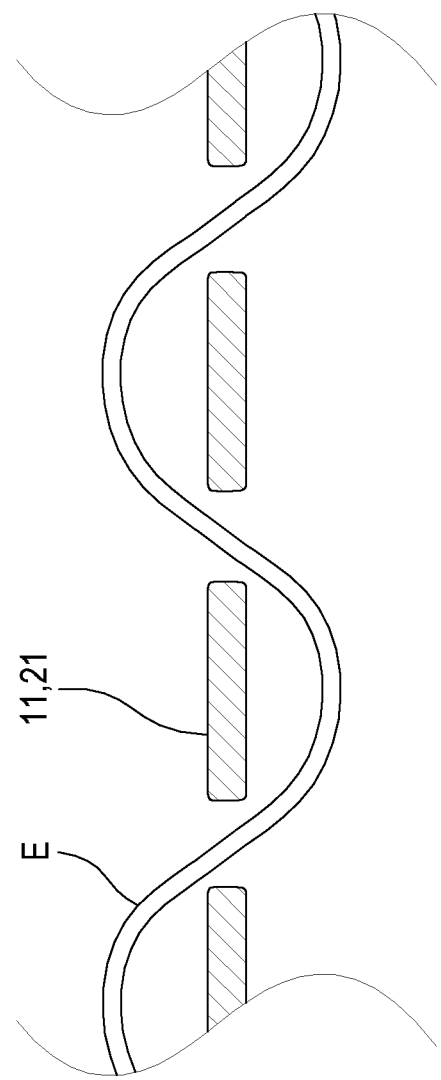

DEVICE FOR MINIMALLY INVASIVE PLASTIC SURGERY LIFT PROCEDURE

REFERENCE TO RELATED APPLICATIONS

The present application claims the benefit of U.S. Provisional Patent Application Ser. No. 61/175,823 filed May 6, 2009 entitled DEVICE FOR MINIMALLY INVASIVE PLASTIC SURGERY LIFT PROCEDURES which is hereby incorporated by reference in its entirety.

BACKGROUND

The present invention relates generally to medical devices configured to be useful in cosmetic surgery and, in particular, to such devices for use in a soft tissue lift procedure.

With an aging population, cosmetic surgery has become a popular choice for many people seeking to improve the look of one or more personal features. For this reason, plastic surgeons have sought to develop methods and devices to support tissue that has lost its natural tension, including tissue of the face, neck, chest, buttocks, or any other area where tissue can sag over time.

One of the more popular procedures involves lifting tissue of the face and neck, which is typically referred to as a rhytidectomy. A rhytidectomy can be performed to improve sagging in the midface, deep creases below the lower eyelids, deep creases along the nose extending to the corner of the mouth, fat that has fallen or is displaced, loss of muscle tone in the lower face that may create jowls, and loose skin and excess fatty deposits under the chin and jaw.

In a traditional rhytidectomy, an incision is made in front of the ear extending up into the hairline. The incision curves around the bottom of the ear and then behind it, usually ending near the hairline on the back of the neck. After the skin incision is made, the skin is separated from the deeper tissues, and the deeper tissues can be tightened with sutures. The skin is then redraped over the lifted tissue.

Modern developments for performing a rhytidectomy involve the use of a medical implant. One such implant is the Endotine Midface™ device. The device includes an enlongated strip of a bioabsorbable material with a fixation platform at one end. The fixation platform is inserted into the face at a point where a lift is desired and is pulled in a backwards direction to lift tissue. The device is then secured to prevent the implant from coming loose.

Soft tissue remains difficult to manipulate by virtue of its inability to hold tension. Moreover, devices used to assist in holding tension can be difficult to surgically implant and, once implanted, can be extremely uncomfortable to a patient. As well, bioabsorbable implants can absorb too quickly, which can result in lifted tissue reverting back to its original position. Accordingly, a need remains for alternative and improved medical devices for use in cosmetic surgery, most notably improved implants for performing a rhytidectomy. The present invention addresses these needs.

SUMMARY OF THE INVENTION

In one aspect, the present invention provides a medical device. The medical device includes an elongate body member having a proximal end, a distal end, and a plurality of gaps defined therebetween. The body member includes at least one tissue engaging member extending laterally therefrom. One or more layers of a collagenous extracellular matrix (ECM) material is associated with the body member. In preferred embodiments, the one or more layers of a collagenous ECM material is woven between the plurality of gaps located along the body member.

In another aspect, the present invention provides a medical device for performing a rhytidectomy. The medical device includes an elongate, semi-rigid body member including a proximal end, a distal end, and a plurality of gaps defined therebetween. The body member includes at least one tissue engaging member extending laterally therefrom. One or more layers of a collagenous extracellular matrix (ECM) material is woven between the plurality of gaps located along the body member.

Further provided by the invention is a method for lifting tissue in a patient. The method includes providing a medical device as described herein and implanting the device into the patient. The device is engaged to lift tissue a desired amount and is secured in place.

The present invention further provides a method for preparing a medical device. The method includes providing an elongate body member having a proximal end, a distal end, and a plurality of gaps defined therebetween. The body member also includes at least one tissue engaging member extending laterally therefrom. One or more layers of a collagenous extracellular matrix (ECM) material is also provided and is associated with the body member. In preferred embodiments, the one or more layers of collagenous ECM material is woven between the plurality of gaps located along the body member.

In another aspect, the present invention provides a method for repositioning soft tissue of a patient. The method includes forcibly relocating a segment of soft tissue from a first position to a second position in such a manner as to introduce tension into the segment of soft tissue and into adjacent soft tissue. The segment of soft tissue is retained in the second position with a tissue engaging member that engages soft tissue proximate to the second position. A remodelable extracellular matrix material is interposed between the segment of soft tissue and soft tissue proximate to the second position. The remodelable material is effective to result in the ingrowth of new tissue of the patient to fuse the segment of soft tissue to the soft tissue proximate to the second position.

Additional embodiments as well as features and advantages of the invention will be apparent from the descriptions herein.

BRIEF DESCRIPTION OF THE DRAWINGS

FIG. 3 depicts a perspective view of a base member that can be used to secure a medical device to a desired location in a patient.

FIGS. 4A-4D depict perspective views of various designs for a base member that can be used to secure a medical device to a desired location in a patient.

FIG. 6 depicts a partial, cross-sectional view of a body member with a material woven through gaps in the body member.

DETAILED DESCRIPTION

Figure 2:
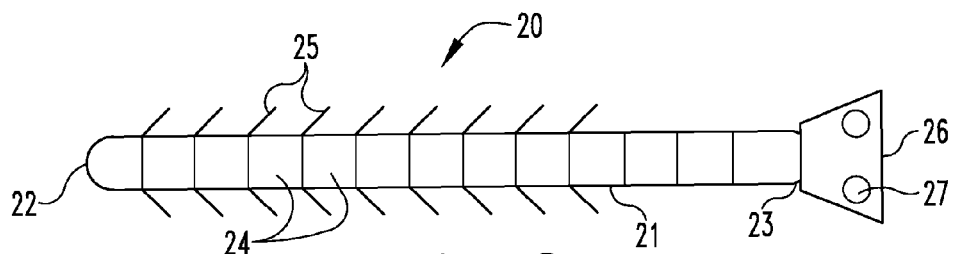
FIG. 2 depicts a perspective view of a medical device of the present invention including a base member.

As noted above, the present invention provides a medical device useful, for example, in cosmetic surgery applications.

The device includes an elongate body member having a proximal end, a distal end, and a plurality of gaps defined therebetween. At least one tissue engaging member is included on the body member and extends laterally therefrom. One or more layers of a collagenous material, preferably a collagenous extracellular matrix (ECM) material, is associated with the body member. While not wishing to be bound by any particular theory, it is believed that the association of a collagenous ECM material with the body member will allow the body member to exist in vivo for a sufficient time so as to substantially prevent the lifted tissue from reverting back to its unlifted position. The collagenous ECM material can also encourage infiltration of the lifted tissue to provide a more permanent result.

Body members for incorporation into the present medical devices are generally elongate and include a proximal end and a distal end. Such members may be made from metallic or non-metallic material, or both. The non-metallic material can suitably be a synthetic polymeric material including, for example, bioresorbable and/or non-bioresorbable plastics. Materials commonly used in body member construction include synthetic polymeric materials such as silicone; low shape memory plastic; a shape-memory plastic or alloy, such as nitinol; and the like. The body member can also be constructed of a collagenous extracellular matrix (ECM) material. Preferably, the body member is constructed of a bioabsorbable polymer, such as poly(lactic-co-glycolic) acid (PLGA). In this respect, the body member can be a rigid body member, a semi-rigid body member, or a soft body member. As used herein, a "rigid body member" refers to a body member comprised of a material which is generally solid throughout and can resist degradation in vivo while a "soft body member" is comprised of a material such as a sponge or a foam. A "semi-rigid body member" generally refers to those materials that are rigid but can become less rigid after implantation into a patient e.g., resorbable materials. Semi-rigid body members are preferably used to construct a body member for the medical devices described herein. Whichever material is chosen it will be preferred that the elongate member exhibit a tensile strength of about 1 pound per square inch to about 10 pounds per square inch and, more preferably, a tensile strength of about 2 pounds per square inch to about 5 pounds per square inch.

A body member for use in the present medical devices can be any suitable shape. For example, the body member can be a cylindrical device having a diameter extending from the proximal end to the distal end. The diameter can be substantially the same throughout the length of the member or can be different. Alternatively, the body member can be substantially planar. In preferred embodiments, the body member is substantially planar.

A body member as described herein can also be any suitable length. For example, a body member can be from about 1 inch to about 24 inches. Preferably, the body member has a length from about 3 inches to about 12 inches, and more preferably from about 5 inches to about 10 inches. These length ranges are meant to serve merely as examples and, as such, are in no way limiting. In this respect, body members having a length smaller than or larger than the ranges indicated above are contemplated for use herein.

A body member as described herein can also be any suitable width. For example, a body member can be from about 0.25 cm to about 2 cm. It will be understood that the desired width of a body member will typically depend on its intended use. A body member used to lift facial tissue will generally be from about 0.25 cm to about 0.75 cm, and preferably 0.5 cm. Of course, the smaller the width of the body member results in the smaller incision required to insert the device into a patient. In this respect, a body member having a width from about 1 mm to about 10 mm is also contemplated. A body member having a width from about 2 mm to about 4 mm is particularly preferred. A body member for use in lifting tissue of the arms, thighs, breasts, buttocks, back and abdomen, for instance, will typically be wider, such as 0.75 cm to about 2.0 cm, and preferably 1.0 cm.

A body member as described herein includes a plurality of gaps. The plurality of gaps extend from the proximal end of the body member towards the distal end. Any number of gaps can be included on the body member. The gaps can be preformed during preparation of the body member or can be formed in the body member after its production. The plurality of gaps can be included in the body member in any suitable pattern. Preferably, the plurality of gaps extend from the proximal end towards the distal end and are spaced evenly from one another. The plurality of gaps can extend from the proximal end to the distal end any desired length and will preferably extend towards the distal end at least about 10%, 20%, 30%, 40% or even at least about 50% or more of the length of the body member. In certain embodiments, the plurality of gaps can extend the entire length of the body member.

A body member as described herein includes at least one tissue engaging member. The tissue engaging member can be constructed of the same material as the body member or can be constructed of a different material. In one embodiment, the tissue engaging member is constructed of a material that absorbs at a faster or slower rate after implantation as compared to the body member. In any case, it is preferred that the tissue engaging member(s) be formed of a bioabsorbable material, such as a bioabsorbable polymer (e.g., PLGA). In such embodiments, the tissue engaging member(s) can retain their general shape and strength for a time sufficient to allow tissue that has been repositioned to fuse at that location.

In a preferred embodiment, the body member includes a plurality of tissue engaging members extending a certain length along the body member. For example, the body member can include tissue engaging members in a generally symmetrical fashion along both sides of the body member and extending at least about 10%, 20%, 30%, 40% or even at least about 50% or more of the length of the body member from the proximal end to the distal end. Preferably, such tissue engaging members are spaced evenly from one another. It will be generally understood by those skilled in the art that the tissue engaging member(s) can be positioned at any location along the length of the body member. As well, any number of tissue engaging members can be included along the length of the body member. Thus, one skilled in the art can use a medical device having the desired length and desired quantity of tissue engaging members for a given procedure.

The tissue engaging member(s) can be any shape and, in certain embodiments, may take the form of barbs or hooks. In preferred embodiments, the tissue engaging member(s) include a rounded tip for contacting tissue. Such adaptations may be included in the body member in areas not associated with a collagenous material or, alternatively, can protrude from the body member and through the collagenous material. The tissue engaging members can be any suitable length and are typically about 2 mm to about 10 mm. Preferably, the tissue engaging members are about 8 mm in length.

The tissue engaging member(s) can extend from the body member in any direction. For example, the tissue engaging member(s) can extend laterally from the body member at an angle of about 45° towards the proximal end or about 45° towards the distal end. Alternatively, the tissue engaging members can extend from the body member at an angle of about 180°. Tissue engaging members can extend at the same angle or different angles from the body member. As well, a tissue engaging member can extend from the body member in a downwards or upwards direction and thus existing in a different plane than the body member. Preferably, the tissue engaging members will each extend laterally from the body member at an angle of about 45° towards the distal end.

A medical device as described herein can be secured in place with a base member. The base member includes at least one slot adapted to receive a medical device. The base member is configured to substantially prevent a medical device from reverting back to its original position after it has been engaged to lift tissue. A base member as described herein is generally configured for use with a medical device including an elongate body member.

As noted herein, a collagenous ECM material can be used in the present invention as a medical device and/or a base member used to secure a device to a body structure. Reconstituted or naturally-derived collagenous materials can be used in the present invention. Such materials that are at least bioresorbable will provide advantage in the present invention, with materials that are bioremodelable and promote cellular invasion and ingrowth providing particular advantage.

Suitable bioremodelable materials can be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more native growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a native bioactive component that induces, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with a device including the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics, thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient.

A non-native bioactive component can be applied to a collagenous extracellular matrix material by any suitable means. Suitable means include, for example, spraying, impregnating, dipping, etc. The non-native bioactive agent can be applied to the collagenous extracellular matrix material either before or after the material is affixed to an elongate member. Similarly, if other chemical or biological components are included in the collagenous extracellular matrix material, the non-native bioactive component can be applied either before, in conjunction with, or after these other components.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

In additional embodiments, medical devices of the invention can include ECM's or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a medical device. Illustratively, the expanded material can be enriched with bioactive components, formed into one or more layers, dried, and then associated with a body member.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material.

After such alkaline treatments, the material can be isolated from the alkaline medium and processed for further use. Illustratively, the collected material can be neutralized and/or rinsed with water to remove the alkalinity from the material, prior to further processing of the material into one or more layers.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression similar to a non-expanded collagenous material.

In certain instances, an elongate member as described herein can be associated with an extracellular matrix material. For example, an elongate body member can be associated with a single layer or multiple layers of material. Thus, in certain embodiments, a single isolated layer of ECM material or a multilaminate ECM construct can be used. Illustrative multilaminate ECM constructs for use in the invention may, for example, have from two to about ten isolated ECM layers laminated together.

Multilaminate ECM constructs for use in the invention can be prepared in any suitable fashion. In this regard, a variety of techniques for laminating ECM layers together can be used. These include, for instance, dehydrothermal bonding under heated, non-heated or lyophilization conditions, using adhesives, glues or other bonding agents, crosslinking with chemical agents or radiation (including UV radiation), or any combination of these with each other or other suitable methods. For additional information as to multilaminate ECM constructs that can be used in the invention, and methods for their preparation, reference may be made for example to U.S. Pat. Nos. 5,711,969, 5,755,791, 5,855,619, 5,955,110, 5,968,096, and to U.S. Patent Publication No. 20050049638.

Medical devices as described herein can include a body member associated with a full or partial covering of a collagenous material, preferably a collagenous ECM material. In this respect, at least about 20% to about 100% of a body member can be associated with a collagenous material. Preferably, at least about 50%, at least about 60%, at least about 70%, at least about 80%, at least about 90%, or even 100% of a body member can be associated with a collagenous material. The collagenous ECM material can be associated with a body member in any suitable fashion. For example, at least one layer of collagenous ECM material can substantially cover the body member. In another embodiment, at least one layer of a collagenous ECM material can be included between consecutive tissue engaging members. In still another embodiment, at least one layer of a collagenous ECM material (E) can be woven through consecutive gaps in the body member (11, 21). (Illustrated in FIG. 6) In some embodiments, the collagenous material is associated in a specific manner with the body member. For example, the collagenous material may be contoured snugly around or completely embed elements of the body member to assist in maintaining the attachment of the collagenous material to the body member. This may avoid, reduce, or simplify the need for other mechanical attachments, such as sutures, to hold the collagenous material to the body member. It may also in some forms provide a specific, relatively fixed association of the collagenous material with the body member or elements thereof. Combinations of these types of associations are also contemplated.

In one embodiment of the invention, the collagenous material is associated with the body member by pressing or otherwise forcing the collagenous material against surfaces of the body member while the collagenous material is in a relatively conformable state, and then converting the collagenous material to a less conformable state. In this manner, the collagenous material while conformable can locally contour to elements of the body member, e.g. elongate portions, and when converted to its relatively less conformable state will maintain that contour to the elements of the body member. As a result, the attachment of the collagenous material to the body member will be facilitated. Further, the collagenous material may have at least some shape memory properties such that if converted back to a conformable state, a contoured relation between the elements of the body member and the collagenous material will still exist.

In preferred aspects of the invention, the collagenous material will be hydratable, and will be relatively more conformable when hydrated than when dried. In this fashion, the collagenous material while in a hydrated state can be forced against a body member sufficiently to locally contour the collagenous material to elements of the body member, and then dried while maintaining that force to achieve an attachment of the collagenous material to the body member. Advantageously, a vacuum pressing operation can be utilized to both force the collagenous material against the elongate member and to dry the entire construct. Lyophilization may also be utilized for this purpose.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and modifications in the illustrated devices, and further applications of the principles of the invention as illustrated therein are herein contemplated as would normally occur to one skilled in the art to which the invention relates are included.

Figure 1:
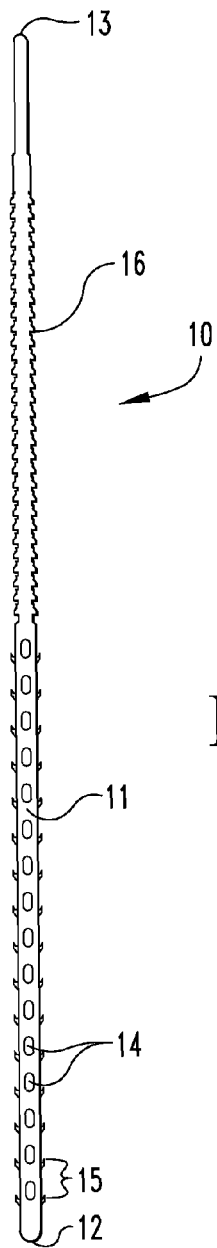
FIG. 1 depicts a perspective view of a medical device of the present invention.
Figure 5A:
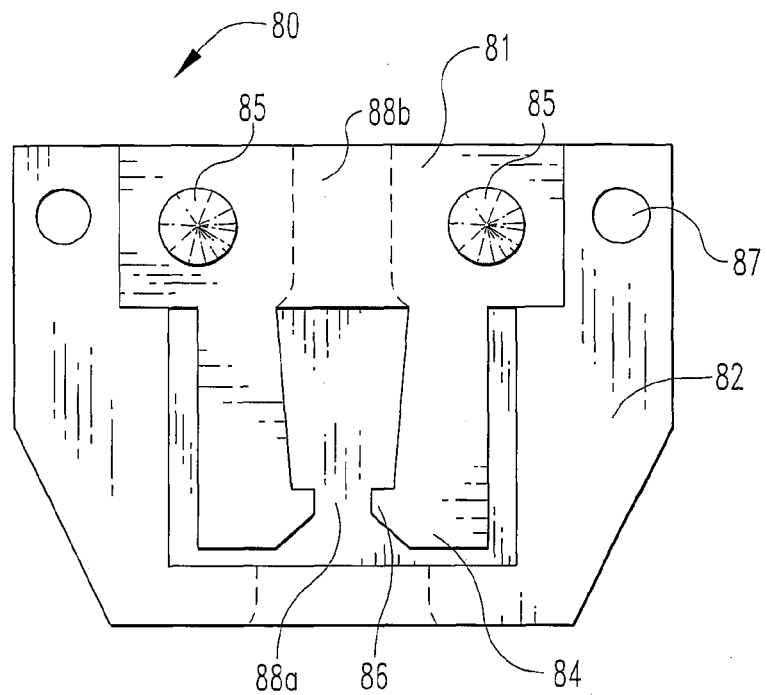
FIGS. 5A-5D depict perspective views of an alternate design for a base member that can be used to secure a medical device to a desired location in a patient.
Figure 5B:
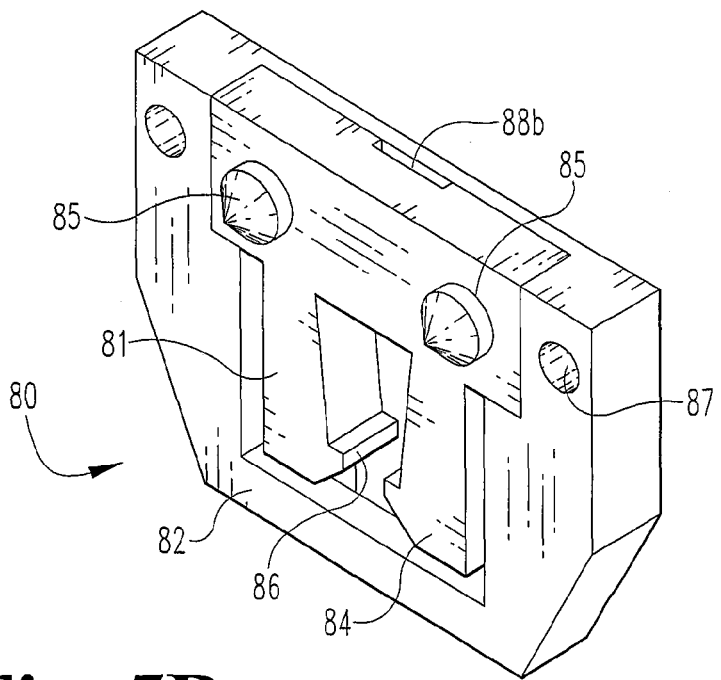
Figure 5C:
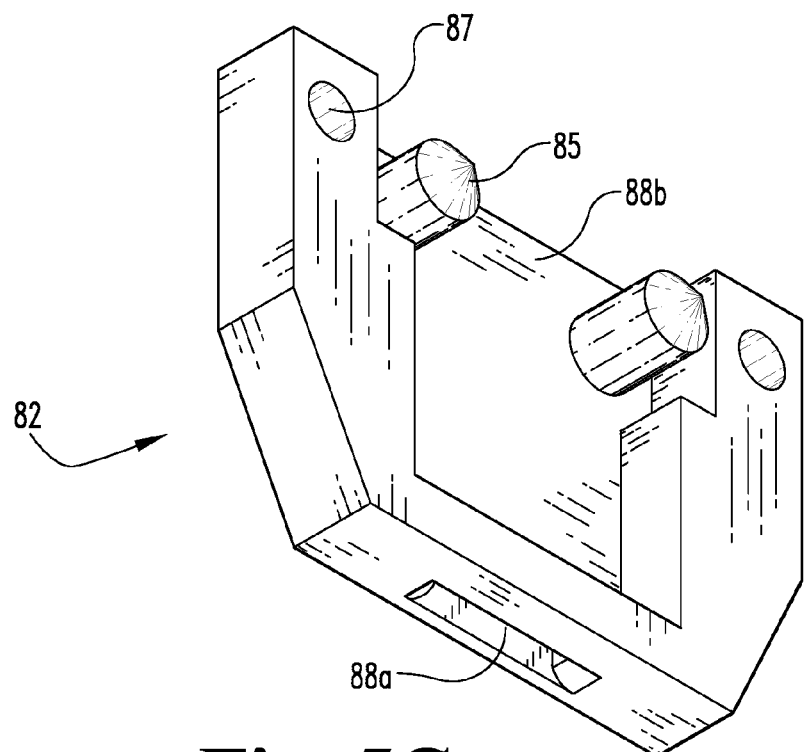
Figure 5D:
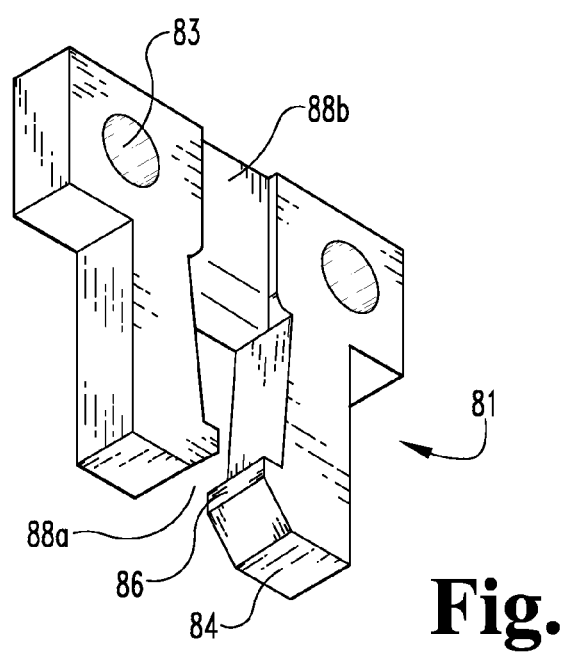

Referring now to the drawings, FIG. 1 illustrates a medical device 10 as described herein. As shown, device 10 includes an elongate body member 11 including a proximal end 12, a distal end 13, and a plurality of gaps 14. The plurality of gaps 14 are spaced along the length of the body member 11 from proximal end 12 towards distal end 13 and extend towards distal end 13 about half of the length of elongate body member 11. Medical device 10 also includes a plurality of tissue engaging members 15. Tissue engaging members 15 are located on both sides of the body member 11 in a generally symmetrical fashion and are spaced evenly from one another. Similar to the plurality of gaps 14, tissue engaging members 15 extend from proximal end 12 towards distal end 13 about half of the length of the body member 11. In this manner, the plurality of gaps 14 and tissue engaging members 15 extend from proximal end 12 towards distal end 13 about the same distance. Medical device 10 further includes notches 16, which can be used to assist the surgeon in manipulating device 10 through tissue. Notches 16 can also assist in retaining device 10 in a desired location once tissue has been lifted.

Referring now to FIG. 2, shown is a medical device 20 including an elongate body member 21 having a proximal end 22, a distal end 23, and a plurality of gaps 24. The plurality of gaps 24 are spaced along the length of the body member 21 between proximal end 22 and distal end 23 and extend towards distal end 23 about 75% of the length of elongate body member 21. Medical device 20 also includes a plurality of tissue engaging members 25. Tissue engaging members 25 are located on both sides of the body member 21 in a generally symmetrical fashion and are spaced evenly from one another. Similar to the plurality of gaps 24, tissue engaging members 25 extend from proximal end 22 towards distal end 23 about 75% of the length of the body member 21. In this manner, the plurality of gaps 24 and tissue engaging members 25 extend from proximal end 22 towards distal end 23 about the same distance. Medical device 20 also includes a base member 26 associated with the distal end 23 of body member 21. Base member 26 includes attachment holes 27 for securing the base member 26 to a body structure. Base member 26 can be formed as part of body member 21 or can be formed separately and later attached to distal end 23 of body member 21. Attachment can involve the use of sutures, staples, and the like, as well as the use of a medical adhesive as generally known in the art, or both.

Turning now to a discussion of a base member, such a base member can be constructed of any suitable material. In preferred embodiments, the base member will be constructed of the same material as the elongate body member, such as a bioabsorbable material or a collagenous extracellular matrix material.

With reference now to FIG. 3, shown is a base member 36 for use in securing an elongate body member to a tissue or boney structure located on or within a patient. Base member 36 is generally square in shape and includes two slots 38 which are generally adapted for an elongate member to pass through. In effect, base member 36 can act like a belt buckle whereby an elongate member can be pulled through slots 38 in a directed D to lift tissue a desired amount.

A base member as used herein is generally configured such that a medical device can be substantially prevented from moving in a forward direction after being moved in a backwards direction D. To accomplish this, a base member, such as base member 36, can include one or more slots that include adaptations to ratchet with adaptations included on a medical device; thereby preventing the medical device from moving in a backwards direction. In other embodiments, a base member can include a pin generally sized and shaped to receive a gap on a medical device. Thus, once the medical device has been pulled through a slot in the base member a desired amount, the closest gap on the device can be placed over the pin so as to prevent the medical device from moving in a forward direction. The pin can be constructed as part of the base member or can be prepared separately and subsequently attached to the base member. Such configurations can also be used together. For example, a base member having one or more slots adapted to ratchet with a medical device can also include a pin generally sized and shaped to receive a gap on the medical device. Other means for preventing the movement of a medical device in a backwards direction would be known to one skilled in the art.

Once the tissue has been lifted, the base member 36 can be secured to a tissue or boney structure through attachment holes 37. Any number of attachment holes 37 can be included on a base member. Preferably, base member 36 is secured to tissue or bone with the use of sutures, staples, and/or screws as generally known in the art. Typically, when securing the base member to tissue, the use of sutures will be preferred, and when the base member is secured to bone, the use of one or more screws will be used.

In one embodiment, the device disclosed above can be used to reposition soft tissue of a patient. The method includes forcibly relocating a segment of soft tissue from a first position to a second position in such a manner as to introduce tension into the segment of soft tissue and into adjacent soft tissue. The segment of soft tissue is retained in the second position with a tissue engaging member that engages soft tissue proximate to the second position. A remodelable extracellular material is interposed between the segment of soft tissue and soft tissue proximate to the second position. The remodelable material is effective to result in the ingrowth of new tissue of the patient to fuse the segment of soft tissue to the soft tissue proximate to the second position. The segment of soft tissue can include any type soft tissue and can include combinations of soft tissue. For example, the segment can include dermal tissue, fatty tissue, or any other soft tissue in need of repositioning. Typically, the soft tissue will be tissue located in the midface area (e.g., cheek area).

With respect to FIGS. 4A-4D, shown are various alternative configurations for a base member suitable for securing a medical device to a body structure as described herein. FIGS. 4A and 4D illustrate a base member 46 and 76, respectively, that are substantially similar to the base member depicted in FIG. 3 with the exception of having differently shaped slots 48 and 78, respectively. FIGS. 4B and 4C illustrate a base member 56 and 66, respectively; having a generally trapezoidal shape and also having differently shaped slots 58 and 68, respectively. It will be understood that base member 46, 56, 66 and 76 each include slots which are generally shaped to receive an elongate member. Thus, a base member can be configured to match the shape of a particular elongate member. In certain embodiments, a base member can also include an extension, such as extension 69, for further securing the base member to a body structure. Any number of extensions can be included on a base member. A variety of other shapes and sizes for a base member can be utilized in the present invention. Base member 46, 56, 66 and 76 thus serve merely as examples and are in no way limiting.

With reference now to FIGS. 5A-5D, shown is an alternate embodiment for a base member. Base member 80 includes an inner portion 81 and an outer portion 82. A front slot 88a is formed through outer portion 82 and extends through inner portion 81 to create a back slot 88b. In this manner, a space is formed extending from front slot 88a through back slot 88b, and this space is generally sized and shaped to receive a medical device as described herein. The base member 80 functions by inserting the distal end of a medical device into front slot 88a such that it passes through arms 84 of the inner portion 81. The distal end of the medical device then exits through back slot 88b, and the surgeon can pull or otherwise direct the medical device in a backwards direction (i.e., away from the tissue to be lifted) to lift tissue a desired amount. The medical device is prevented from moving in a forward direction (i.e., towards the tissue to be lifted) by notches 86 of arms 84. Notches 86 are configured to ratchet with adaptations located on a medical device such that the medical device can only move towards slot 88b. Arms 84 are thus initially not spaced far enough apart for a medical device having adaptations to pass through. However, as a medical device is forced through front slot 88a towards back slot 88b, the distance between arms 84 can be caused to increase by adaptations on the medical device forcing arms 84 towards outer portion 82; thereby allowing the medical device to pass through. As one set of adaptations passes by notches 86, arms 84 automatically revert back to a width whereby the medical device cannot pass. Thus, one set of adaptations remains on the back side of notches 86 while another set of adaptations is present on the front side of notches 86. As such, a medical device becomes temporarily locked in place until another set of adaptations is forced through notches 86 towards back slot 88b. If desired, a means for releasing the arms 84 of inner portion 81 can be included on the base member. This can be included in the event a medical device is engaged to lift tissue too much, and the surgeon needs to release arms 84 such that a medical device can be moved back through front slot 88a a desired amount. Such a means would force arms 84 outwards toward outer portion 82 such that the width between arms 84 is increased to allow the medical device containing adaptations to pass through notches 86. Once the medical device has been moved through front slot 88*a*, the surgeon can disengaged the means for releasing arms 84; thereby locking the medical device in place with one set of adaptations on the back side of notches 86 and another set of adaptations on the front side of notches 86.

As shown in FIGS. 5A-5D, base member 80 is constructed of two portions. Outer portion 82 includes extensions 85, which are generally sized and shaped to receive holes 83 located on inner portion 81. Outer portion 82 also includes attachment holes 87, which are generally adapted to assist in securing the base member to a body structure. This can be accomplished with the use of staples, sutures, and the like as discussed previously. In practice, outer portion 82 can be secured to a body structure through holes 87. Inner portion 81 can then be placed over outer portion 82 by placing holes 83 of inner portion 81 over extension 85 of outer portion 82. Alternatively, inner portion 81 can be associated with outer portion 82 prior to securing outer portion 82 to a body structure. The association of inner portion 81 to outer portion 82 can be temporary or can be permanent. In one embodiment, inner portion 81 can remain associated with outer portion 82 until a medical device has been implanted for a period of time sufficient for the medical device to become infiltrated with tissue. At this point, the medical device is secured in place such that inner portion 81 and/or outer portion 82 can be removed.

A base member can include any number of slots. As shown in FIGS. 3 and 4A-4D, base member can include two slots. In other embodiments, it is contemplated for a base member to include a single slot, three slots, four slots, five slots, or even six or more slots. Preferably, a base member will include two slots so as to preserve the "belt-buckle" effect of engaging a medical device received therein to lift tissue a desired amount. The one or more slots can be formed as part of the base member or can be cut or otherwise created in the base member after the base member is formed.

Devices of the invention, such as devices 10 and 20, are desirably adapted for insertion within the head and neck (e.g., facial structures, such as eyebrows, jowls, laugh lines, neck and midface), but can be used to lift tissue located at any part of the body or mammal, preferably a human. For example, a medical device as described herein can be used for cosmetic lift procedures in the arms, thighs, breasts, buttocks, back and abdomen.

It is contemplated for any number of surfaces and/or structures contained within the patient, including muscle, fat, skin and/or fascia, to be lifted by a medical device. If more than one surface and/or structure requires lifting, a medical device can be used to lift each surface and/or structure and can be implanted either individually or together. In preferred embodiments, if more than one surface and/or structure is in need of lifting, each structure will be treated at the same time so as to allow for better results, particularly in post-surgical applications where there is a high risk of tissue collapse. In one embodiment, one device can be implanted in a deep fat layer while a second medical device can be implanted superficially. In any case, the medical devices described herein are generally adapted to lift soft tissue.

In order to deliver the medical device to a patient, an introducer can be implemented. An introducer can be a generally rigid material having a lumen. The lumen will be of a shape such that the medical device can be received therein but will not be of a shape that promotes the twisting or turning of the medical device while it is in the lumen. In this way, the lumen of the introducer will typically be substantially the same shape as the medical device but will be sized slightly larger to allow a medical device to be received therein. Thus, the lumen can be flat and/or can have a ellipse cross-section depending on the shape of the medical device. The introducer can be constructed of any suitable rigid or semi-rigid material, such as a smooth plastic material or stainless steel. Preferably, the introducer will be constructed so as to minimize tissue damage during implantation of the medical device. In this respect, the proximal end of the introducer will preferably be rounded or otherwise shaped to reduce damage to surrounding tissue. The introducer can include one or more perforations to allow for hydration and/or sterilization. Moreover, the medical device can be packaged and sterilized within the introducer such that the end user does not have to load the introducer with the medical device prior to use.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. In addition, all publications cited herein are indicative of the abilities of those of ordinary skill in the art and are hereby incorporated by reference in their entirety as if individually incorporated by reference and fully set forth.

What is claimed is:

1. A medical device, said device comprising:
   an elongate body member having a first side, a second side, a proximal end, a distal end, and a plurality of gaps defined therebetween;
   a plurality of tissue engaging members extending laterally from said elongate body member, including a first tissue engaging member extending laterally from said elongate body member at a first location and a second tissue engaging member extending laterally from said elongate body member at a second location; and
   one or more layers of a collagenous extracellular matrix (ECM) material woven through a first gap and a second gap of said plurality of gaps in said elongate body member, wherein at least a portion of said one or more layers of collagenous ECM material extends from said first side towards said second side through said first gap and from said second side towards said first side through said second gap; and wherein at least one gap of said plurality of gaps is located at or between said first location and said second location.

2. The medical device of claim 1, wherein said body member is comprised of a collagenous ECM material.

3. The medical device of claim 1, wherein said body member is comprised of a bioabsorbable polymer.

4. The medical device of claim 3, wherein said body member is poly(lactic-co-glycolic) acid.

5. The medical device of claim 1, wherein said device is configured for implantation into the face of a mammal.

6. The medical device of claim 1, wherein said body member further comprises a base member.

7. The medical device of claim 6, wherein said base member comprises one or more suture holes.

8. The medical device of claim 1, wherein at least about 50% of said body member is associated with a collagenous ECM material.

9. The medical device of claim 1, wherein said one or more layers of collagenous ECM material includes one or more native or non-native bioactive components.

10. The medical device of claim 9, wherein said one or more bioactive components is a growth factor.

11. The medical device of claim 10, wherein said growth factor is fibroblast growth factor-2 (FGF-2).

12. The medical device of claim 1, wherein said device comprises at least two layers of said collagenous ECM material, wherein the layers are associated with one another to form a laminate of ECM material.

13. The medical device of claim 12, wherein said laminate of collagenous ECM material is lyophilized.

14. The medical device of claim 1, wherein said at least one tissue engaging member includes a rounded tip for contacting tissue.

15. The medical device of claim 1, wherein said device has a width of about 2 millimeters to about 4 millimeters.

16. The medical device of claim 1, wherein said at least one tissue engaging member is constructed of a different material than the material used to construct the body member.

17. The medical device of claim 16, wherein the material used to construct the at least one tissue engaging member absorbs at a faster rate as compared to the material used to construct the body member.

18. The medical device of claim 1, wherein said device has a length of about 1 inch to about 24 inches.

19. The medical device of claim 1, wherein said medical device has a tensile strength of at about 2 pounds per square inch to about 5 pounds per square inch.

20. The medical device of claim 1, wherein said one or more layers of collagenous ECM material comprises submucosa.

21. The medical device of claim 20, wherein said submucosa is intestinal, urinary bladder or stomach submucosa.

22. The medical device of claim 21, wherein said submucosa is small intestinal submucosa (SIS).

23. The medical device of claim 1, wherein said plurality of gaps extend continuously along a length of said elongate body member.

24. The medical device of claim 1, wherein said plurality of gaps are spaced evenly from one another.

25. A method for lifting tissue in a patient, comprising:
providing a medical device of claim 1;
implanting said medical device into the patient; and
engaging said medical device so as to lift tissue a desired amount.

26. A medical device for performing a rhytidectomy, said device comprising:
an elongate body member including a first side, a second side, a proximal end, a distal end, and a plurality of gaps therebetween wherein said body member is formed from a bioabsorbable material; and
one or more layers of a collagenous extracellular matrix (ECM) material,
wherein said one or more layers of collagenous ECM material is woven through a first gap and a second gap of the plurality of gaps of the elongate body member with a portion of said one or more layers of collagenous ECM material extending through said first gap from said first side towards said second side and through said second gap from said second side towards said first side.

27. A medical device comprising:
an elongate body member having a proximal end, a distal end, and a plurality of gaps defined therebetween along a segment of the elongate body member;
a first tissue engaging member extending from said segment at a first location and a second tissue engaging member extending from said segment at a second location; and
one or more layers of a collagenous extracellular matrix (ECM) material; and
wherein at least a portion of said elongate body member is associated with said one or more layers of collagenous ECM material by said one or more layers of collagenous ECM material being woven through the gaps of said elongate body member with said one or more layers of collagenous ECM material extending in a first direction through a first gap of said plurality of gaps and extending in a second direction through a second gap of said plurality of gaps; and
wherein at least one of said gaps of said plurality of gaps is located at or between said first location and said second location.

28. The medical device of claim 27, further comprising a base member.

29. The medical device of claim 28, wherein said elongate body member further comprises a plurality of notches configured to engage said base member.

30. The medical device of claim 27, wherein said tissue engaging members extend laterally from said elongate body member.

31. The medical device of claim 27, wherein said body member is comprised of a collagenous ECM material.

* * * * *